United States Patent [19]

Gysi et al.

[11] Patent Number: 5,613,713
[45] Date of Patent: Mar. 25, 1997

[54] ARRANGEMENT FOR CLEANING A CONTAINER TESTING APPARATUS

[75] Inventors: Peter Gysi, Bellikon; Theo Huesser, Rudolfstetten; Daniel Wildmann, Dielsdorf, all of Switzerland

[73] Assignee: Elpatronic AG, Zug, Switzerland

[21] Appl. No.: 390,634

[22] Filed: Feb. 17, 1995

[30] Foreign Application Priority Data

Mar. 17, 1994 [CH] Switzerland ............................ 0792/94

[51] Int. Cl.$^6$ .................................................. F16L 25/00
[52] U.S. Cl. .............................. 285/12; 285/23; 285/119; 134/22.11; 134/166 C; 134/169 R
[58] Field of Search ............................ 285/12, 119, 132, 285/23; 134/166 R, 166 C, 167 C, 169 R, 22.11, 22.12, 84

[56] References Cited

U.S. PATENT DOCUMENTS

| | | | |
|---|---|---|---|
| 3,430,639 | 3/1969 | Roberts | 134/169 |
| 3,907,011 | 9/1975 | Edmunds | 134/166 R X |
| 3,991,797 | 11/1976 | Uth | 134/166 C X |
| 4,168,677 | 9/1979 | Brown | 134/166 R X |
| 4,559,961 | 12/1985 | Anderson et al. | 134/166 |
| 4,718,465 | 1/1988 | Dugan | 134/166 R X |
| 4,991,610 | 2/1991 | Huben et al. | 134/169 R |
| 5,168,720 | 12/1992 | Keltner | 285/12 X |
| 5,343,907 | 9/1994 | Wagner | 134/166 C X |
| 5,433,163 | 7/1995 | McKiernan | 285/12 X |

FOREIGN PATENT DOCUMENTS

| | | | |
|---|---|---|---|
| 0120171 | 10/1984 | European Pat. Off. . | |
| 0534096 | 3/1993 | European Pat. Off. . | |
| 1598848 | 8/1970 | Germany . | |
| 5106772 | 4/1993 | Japan | 285/132 |
| 150064 | 12/1931 | Switzerland | 285/132 |

Primary Examiner—Dave W. Arola
Attorney, Agent, or Firm—McCormick, Paulding & Huber

[57] ABSTRACT

On a bottle testing apparatus which has a plurality of sampling tubes which can be lowered into the bottles, the said tubes are individually detachable for cleaning. Hence they can be quickly and easily replaced with clean tubes. In addition, an adaptor is provided by means of which a cleaning fluid can be passed through the pipes of the apparatus.

2 Claims, 3 Drawing Sheets

ARRANGEMENT FOR CLEANING A CONTAINER TESTING APPARATUS

BACKGROUND OF THE INVENTION

The invention relates to processes for cleaning a container testing apparatus having gas sampling elements which can be lowered into the containers and a distributor device for successively dispensing the gas samples withdrawn from the containers to an analyzing instrument. The invention also relates to a container testing apparatus with a plurality of sampling elements which can be lowered into the container and an arrangement for cleaning a container testing apparatus having a stationary distributor head part and a moving distributor head part and pipes leading from said moving part to sampling elements which can be lowered into containers for testing.

With returnable bottles, in particular with plastic bottles, such as PET bottles, which cannot be washed at high temperatures, the problem arises that contamination must be reliably detected in order that contaminated bottles can be removed and/or diverted from refilling. In particular, it is necessary to be able to detect returned bottles which have been used by individual users for potentially dangerous substances (poisons, solvents). It is an already known procedure to take a gas sample from each bottle for this purpose and to analyse the sample by a suitable method, e.g. by photoionization detection (PID) or mass spectroscopy. The presence of even small traces of undesired substances in the bottle and/or in the plastic material can be detected in this way. Industrial testing apparatus with a high bottle throughput (of e.g. 250 to 700 bottles per minute) which test the bottles in this manner are available on the market.

It has been found that the cleaning of a testing apparatus of this kind, possessing a large number of sampling tubes for withdrawing the gas samples, is a laborious process involving relatively extended stoppage times. Nevertheless frequent cleaning is necessary in order that sensitive detection of foreign substances can actually be achieved.

SUMMARY OF THE INVENTION

The invention therefore addresses the object of facilitating the cleaning of container testing apparatus. This is achieved by the process in which a cleaning medium is passed through the distributor device by means of an adaptor mounted on the distributor device, and the gas sampling elements are at least partially dismantled and cleaned separately and also, with the container testing apparatus in which the sampling elements each comprise a sampling tube which is attached in such a manner that it can be released without the use of a tool and with the arrangement having an adaptor part which can be mounted on the container testing apparatus in place of the stationary distributor head part. The adaptor part has a connection for supplying at least one fluid and a channel which is in communication with the connection and which, when the adaptor part is fitted, is in communication with at least some of the pipes via the moving distributor head part.

According to a first aspect of the invention, the object is attained by providing each of the sampling units with a releasably attached sampling tube.

This makes it possible to separate the sampling tubes from the testing apparatus for cleaning purposes, and to fit precleaned and therefore uncontaminated sampling tubes, within an extremely short time. The sampling tubes which have been removed can then be cleaned without time pressure, and hence thoroughly, and are then available for the next changeover. This in itself enables the cleaning of sampling tubes, and/or the fitting of clean tubes, to be carried out every 2 to 3 days without long and costly stoppages.

In accordance with a further aspect of the invention, the object is achieved by an arrangement for cleaning a testing apparatus which allows simple cleaning of the parts connected to the sampling tube which conveys the gas to the testing instrument.

This arrangement allows simple flushing and drying of the principal pipes and passageways of a testing apparatus.

BRIEF DESCRIPTION OF THE DRAWINGS

Embodiments of the invention will now be explained in detail by way of example with reference to the drawings, in which.

DESCRIPTION OF THE PREFERRED EMBODIMENTS

Figure 1:
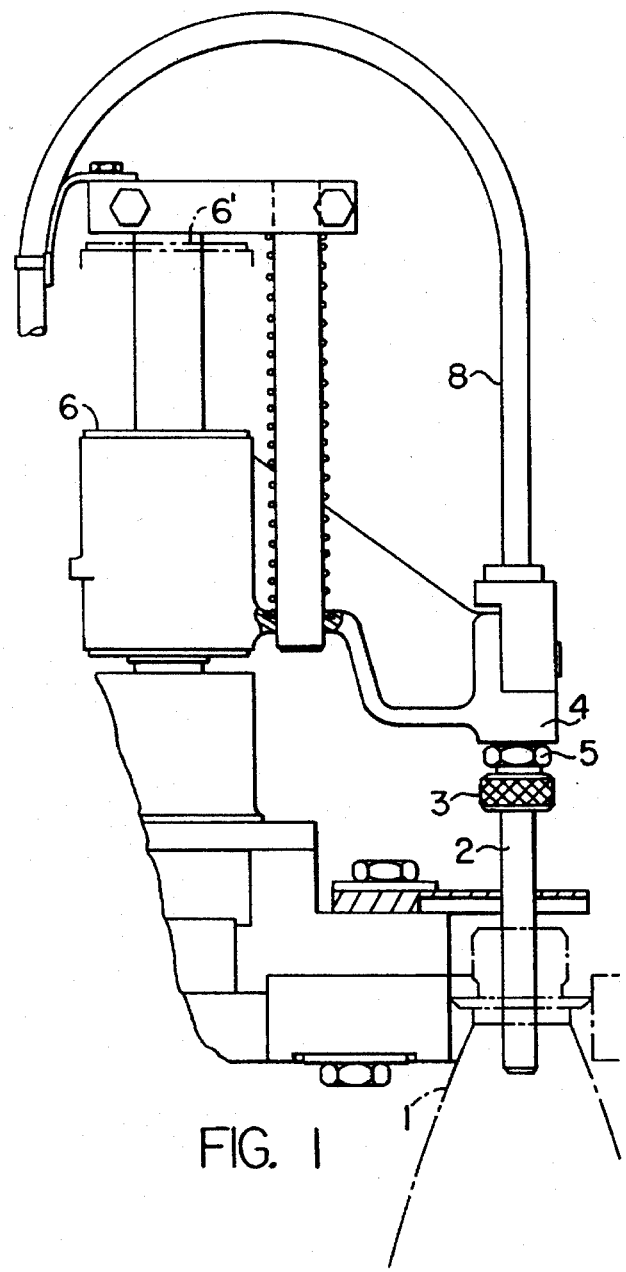
FIG. 1 is a schematic partial view of a bottle testing apparatus.

FIG. 1 shows part of a bottle testing apparatus which is constructed e.g. in the form of a conveyor carousel carrying a large number of bottles. In FIG. 1, only part of one bottle 1 is indicated in chain-dotted outline. Above each bottle holder position on the carousel, a sampling tube 2 for withdrawing gas from the bottle 1 is mounted on a movable slide 6. In FIG. 1 the slide 6 is shown with the sampling tube 2 dipping into the bottle 1 for the withdrawal of gas. In an upper slide position, represented at 6' by a fragmentary view of the top of the slide, the sampling tube 2 is lifted out of the bottle 1. Movement of the slide is effected e.g. by means of a cam against the action of a spring. It is of course also possible to move the bottle rather than the sampling tube. When the bottle 1 enters a respective holder on the carousel, the slide is in its upper position. The slide together with the sampling tube is then lowered and gas is withdrawn from the bottle 1 while the latter remains in the carousel. The withdrawn gas passes via a hose 8 to a distributor head which successively switches the gas withdrawn from the bottles present in the carousel, as individual gas samples, to one or more analysing instruments. When the bottle has completed its time in the carousel, the slide 6 is raised to the position 6' and the bottle leaves the carousel. The corresponding bottle holder is then able to receive another bottle.

In this instance the sampling tube 2 is releasably attached to a holder 4,5 which is fixed to the slide. The releasable attachment, e.g. by means of a cap nut 3, enables each sampling tube to be rapidly released from the slide 6 and replaced with a clean tube 2. As a result, the down time for the testing apparatus is short. The tubes 2 which have been released can then be cleaned at leisure.

Figure 2:
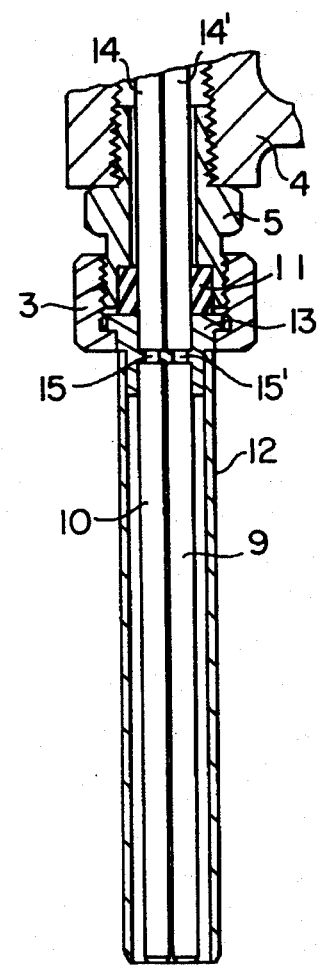
FIG. 2 is a schematic sectional view of the sampling tube in FIG. 1.

FIG. 2 shows a gas sampling tube 2 and its attachment to the holder 5 on the slide extension arm 4. The gas sampling tube 2 has an outer, generally cylindrical, sleeve 12. The actual extraction tube 10 for the gas is arranged inside this sleeve 12. The extraction tube 10 is coupled to a flexible pipe 14 which extends inside the hose 8 and which conveys the gas to the distributor head.

The extraction tube 10 is permanently fixed inside the gas sampling tube 2 and is replaced along with it. The extraction tube is attached by being fixed in an end spigot 13 which is connected to the sleeve 12, e.g. by soldering, bonding, or welding. The tube 10 communicates with the pipe 14 via a bore 15 in the spigot 13. An air injection tube 9 is also fixed inside the sampling tube 2 by means of the end spigot 13 attached to the sleeve 12. To assist the withdrawal of a representative gas sample, air is blown into the bottle 1 through a pipe 14' in the hose 8, which communicates with the tube 9 in the spigot 13 via a bore 15' in the spigot 13 which is common to the pipe 14' and to the tube 9. Hence the tubes 9 and 10 are removed together from the holder 5 along with the sleeve 12.

The gas sampling tube 2, comprising the sleeve 12 and the tubes 9,10, is attached to the holder 5 by means of a cap nut 3 which is preferably arranged to be tightened and loosened without the use of a tool. This cap nut engages with a peripheral flange of the spigot 13 connected to the sleeve 12. When the cap nut 3 is tightened on the holder 5 to secure the gas sampling tube 2 to the slide 6, a rubber seal 11 which projects from the holder 5 is compressed by the end face of the spigot 13.

The sampling apparatus also contains a heater element (which is not visible in FIG. 2 since it lies behind the tubes 9,10) to prevent condensation, especially on the extraction tube 10. This heater element is preferably permanently installed in the holder 5 and/or slide extension arm, and is not replaced along with the individual sampling tube. However, space is provided in the sampling tube for this heater element, which is usually in the form of a rod, and the spigot 13 has a corresponding bore to enable it to pass through.

Figure 3A:
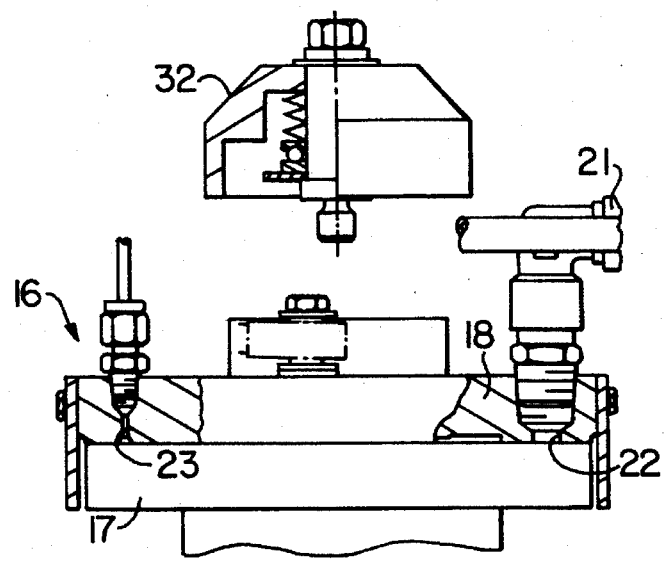
FIG. 3A is an exploded view of the distributor head.
Figure 3:
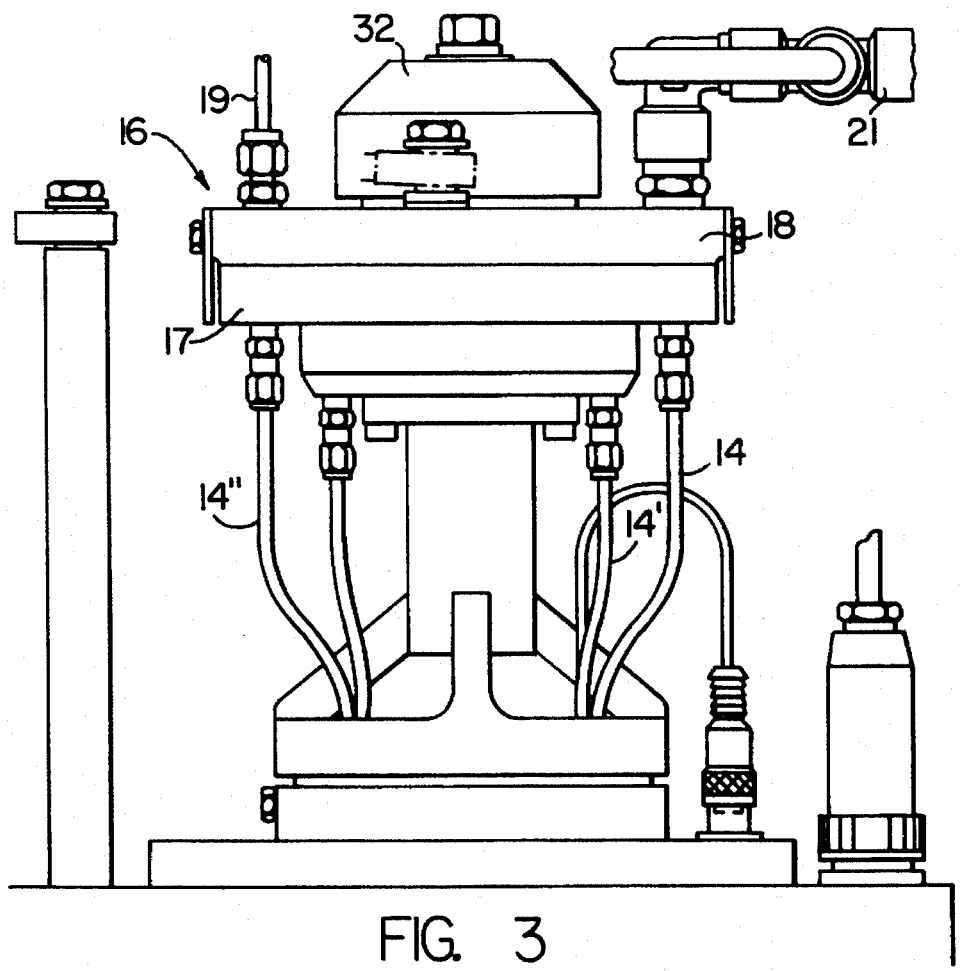
FIG. 3 is a schematic view of the distributor head and carousel of the testing apparatus.

FIG. 3 shows a further part of the testing apparatus, with the abovementioned distributor head 16, located on the central axis of the carousel in this example. The distributor head comprises a rotating part 17 and a stationary part 18. The rotating part 17 is mounted on and is moved with the carousel. These parts are pressed together by a central pressure bell 32. In FIG. 3A, the parts 17,18 and 32 have been exploded and partially cutaway for the sake of clarity. Connected to the rotating part 17 are the individual pipes which are combined inside the hose 8 in FIG. 1, namely in each case the pipe 14 conveying the gas sample to the distributor head and the pipe 14' conveying compressed air to the bottle. Inside the distributor head 16 all the gas samples are drawn through a central suction pipe 21, one of the gas samples in each case passing via a pipe 19 to the analysing instrument, e.g. to a mass spectrometer. For this purpose, the stationary part 18 of the distributor head contains an annular channel 22 which is interrupted at one point. An isolating passageway 23 is provided at this point. All the pipes 14 except one are in communication with the channel 22. A single pipe at the position indicated by the reference 14" is in communication with the passageway 23 at any given time, and the gas sample from the pipe at this position passes into the pipe 19 and thence to the analysing instrument. As the moving part 17 rotates, each pipe 14 arrives in succession in the position 14" in FIG. 3, so that each gas sample passes separately and in succession to the analysing instrument.

Figure 4:
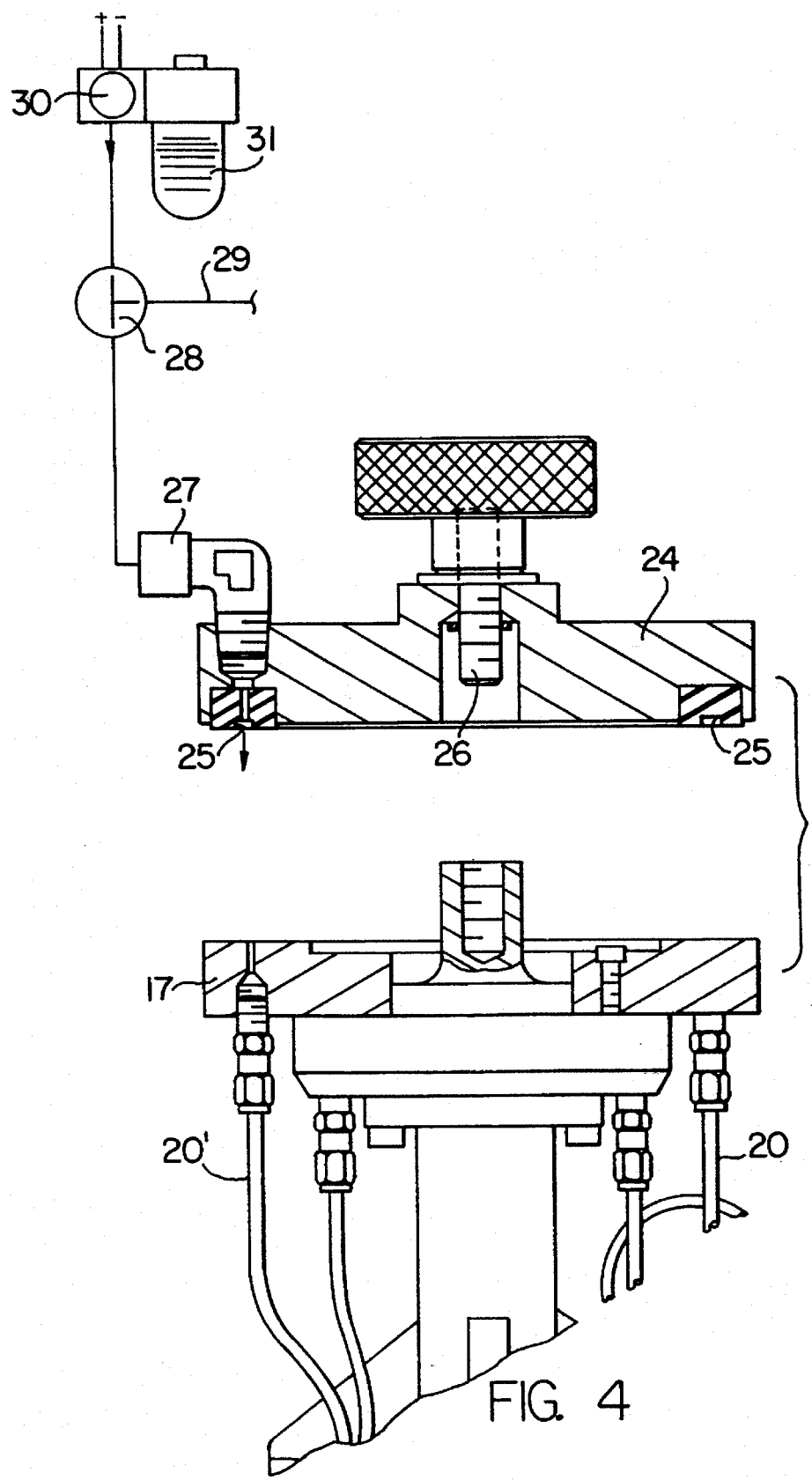
FIG. 4 is, likewise in schematic and partly cut-away form, a view of the testing apparatus with the adaptor part for use when cleaning the apparatus.

FIG. 4 shows the lower part of the distributor head in partly cut-away representation, the same elements being designated by the same reference symbols as in FIG. 3.

Above the moving part 17 of the distributor head, an adaptor 24 which can be screwed onto the part 17 is shown in an as yet unconnected position. The connection may be made by means of the screw 26. The adaptor is used when cleaning the pipes 14 and the moving part 17, with the carousel stationary. For this purpose the adaptor 24 has a connection 27 to which a pipe supplying cleaning fluid under pressure or compressed air can be connected (this pipe is only schematically represented in the drawing). An electrically driven pump 30 (likewise only schematically represented) and a cleaning fluid tank 31 supplying this pump are for example provided for this purpose. Instead of the cleaning fluid, compressed air from a line 29 can be fed to the connection 27 via a two-way valve 28.

On its surface facing the moving part 17, the adaptor has a channel 2B through which the cleaning fluid, or compressed air as the case may be, can be conveyed to all pipes 14. In this case, the channel 2S is circular. Alternatively, a semicircular channel 25 may be provided. In this case, the adaptor must be mounted a second time after being rotated through 180°. The advantage of the semicircular arrangement is that containers (bottles) need to be placed at only half the carousel positions to catch the cleaning fluid, which may be advantageous for reasons of accessibility, and the number of containers required.

Cleaning with the adaptor results in quick and thorough cleaning of all major parts. Such cleaning may for example be carried out at monthly intervals. A further advantage of this method of cleaning is that when cleaning fluid is being forced through the system under pressure and/or when compressed air is subsequently connected, escapes of cleaning fluid or cleaning fluid/compressed air mixture make it possible to pinpoint leaks which are difficult to detect in operation (when surrounding air is sucked in). Accordingly, the adaptor can also be used at other times for detecting any leaks which may be present.

We claim:

1. Arrangement for cleaning a container testing apparatus, the apparatus including a rotating carousel, a stationary distributor head part, and a rotating distributor head part in fluid communication with the stationary distributor head part, the rotating distributor head part being mounted on and rotated by the carousel of the container testing apparatus and coupled to pipes extending into containers to extract gas samples from the containers and to distribute the gas samples from the containers and through the pipes to an analysis instrument associated with the stationary distributor head part for testing the containers for contamination, the arrangement comprising:

an adaptor part for cleaning the pipes and the rotating distributor head part of the container testing apparatus when off-line during a cleaning cycle, the adaptor part being mounted on the rotating part in place of the stationary distributor head part, the adaptor part including a connection for fluid communication with a cleaning source, the adaptor and the rotating distributor head parts cooperating with one another to define an enclosed fluid channel communicating with the connection for the cleaning source and with the pipes to provide a fluid path from the cleaning source to the pipes.

2. Arrangement according to claim 1, characterized in that the channel extends in a semicircular configuration.

* * * * *